United States Patent
Deck et al.

(10) Patent No.: US 7,391,509 B1
(45) Date of Patent: Jun. 24, 2008

(54) DEVICES AND METHODS FOR MULTI-MODE ANALYTICAL MICROSCOPY, IN PARTICULAR FOR UV FLUORESCENCE AND RAMAN ANALYSIS OF SAMPLES

(75) Inventors: Francis J. Deck, Madison, WI (US); Mark H. Wall, Madison, WI (US); Joe Hodkiewicz, Madison, WI (US)

(73) Assignee: Thermo Electron Scientific Instruments LLC, Madison, WI (US)

( * ) Notice: Subject to any disclaimer, the term of this patent is extended or adjusted under 35 U.S.C. 154(b) by 308 days.

(21) Appl. No.: 11/345,764

(22) Filed: Feb. 2, 2006

(51) Int. Cl.
*G01B 9/02* (2006.01)
(52) U.S. Cl. ....................... 356/73
(58) Field of Classification Search ........................ None
See application file for complete search history.

(56) References Cited

U.S. PATENT DOCUMENTS 6,661,509 B2   12/2003   Deck et al.

2007/0070349 A1*   3/2007   Harris et al. ................ 356/417

\* cited by examiner

*Primary Examiner*—Tu T Nguyen
(74) *Attorney, Agent, or Firm*—DeWitt Ross & Stevens; Michael C. Staggs

(57) ABSTRACT

An analytical microscope provides both UV fluorescence imaging and spectroscopic analysis of a sample with use of the same light collection element (objective lens or other optical element). An incident UV light beam travels to the sample via a dark field illumination path about the periphery of the collection lens, with the collection lens then collecting the emitted light from the sample and forwarding it to an eyepiece and/or camera for viewing. The sample is also illuminated with a laser through the collection lens to generate Raman emissions, which are then collected through the same collection lens and provided to a spectrograph for wavelength identification. Use of the same collection lens for both imaging and spectroscopic analysis better ensures that any imaged regions of interest on the sample are the same as those being spectroscopically analyzed.

23 Claims, 1 Drawing Sheet

THE FIGURE
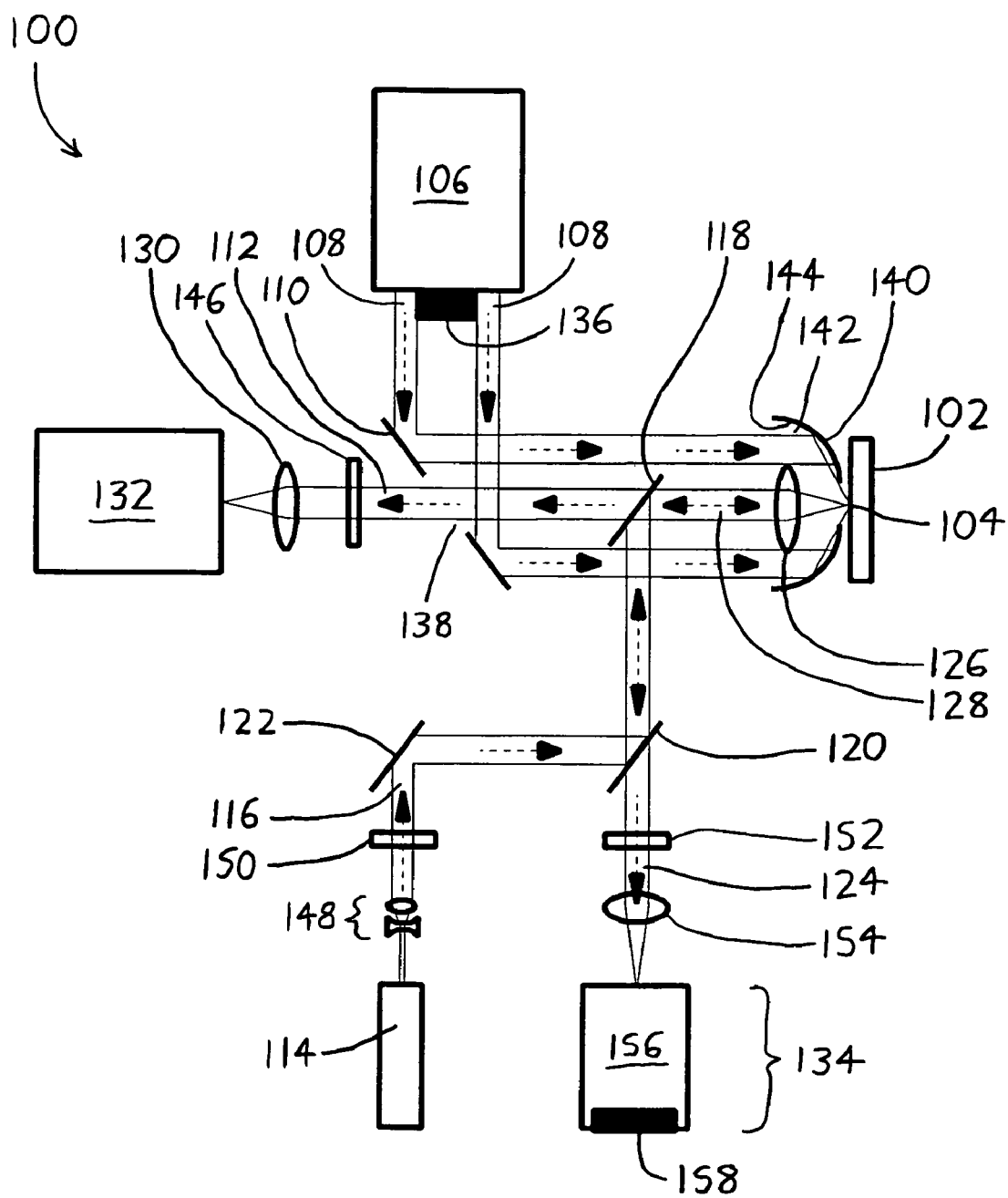

DEVICES AND METHODS FOR MULTI-MODE ANALYTICAL MICROSCOPY, IN PARTICULAR FOR UV FLUORESCENCE AND RAMAN ANALYSIS OF SAMPLES

FIELD OF THE INVENTION

This document concerns an invention relating generally to analytical microscopy, and more specifically to analytical microscopes which provide more than one mode of viewing/analysis of a sample (e.g., providing both microscopic viewing of the sample as well as spectrometric analysis of the sample).

BACKGROUND OF THE INVENTION

When analyzing materials, it is often useful to use a multi-mode analytical microscope which allows conventional forms of microscopic imaging of the material in question in combination with some other form of imaging/analysis. As an example, U.S. Pat. No. 6,661,509 to Deck et al. describes a multi-mode analytical microscope which provides both conventional optical microscopy (i.e., magnified viewing of microscopic sections of a sample) with Raman spectrometric analysis (i.e., analysis of laser light scattered by the sample, which can provide information about the composition of the sample). Other types of multi-mode microscopes may provide additional or alternative types of microscopic viewing (e.g., fluorescence microscopy, which allows viewing of wavelength-shifted light emitted from a sample) with additional or alternative types of sample analysis (e.g., spectrometric analysis of light emitted and/or scattered by a sample from incident light in infrared, visible, and/or ultraviolet wavelengths).

While multi-mode analytical microscopes can often be constructed by "superimposing" features of different microscopes, spectrometers, and similar instruments—in other words, by simply combining the components of the different instruments about the sample mount/stage so that the different instruments may be used together—such a construction can be expensive and inefficient, with the combined instruments providing redundant and/or interfering components. As an example, it is desirable to have the optical elements (lenses, mirrors, etc.) of one instrument also at least partially serve as the optical elements of the other instrument, thereby allowing a reduction in cost and physical size of the combined instrument. However, this may not be feasible because optical elements designed for use in visible ("Vis") wavelength ranges, ultraviolet (UV) wavelength ranges, and infrared (IR) wavelength ranges are generally not appropriate for use at other ones of the ranges: the different instruments may effectively have incompatible optics. Thus, it is often necessary to provide components for each of the combined instruments, and to possibly move/exchange these components when changing the multi-mode instrument from one mode of viewing/analysis to another. This can lead to greater instrument costs and size, as well as added complexity when performing viewing/analysis techniques. In particular, the need to switch optics can lead to difficulties in accurate viewing and analysis. To illustrate, after microscopically viewing some specific region of interest on the sample, it can be problematic to switch optics to then allow spectrometric analysis of the same region on the sample because of difficulties in attaining the same alignment of the microscopic and spectrometric optics. It would therefore be useful to have available additional multi-mode analytical microscopy devices and methods which eliminate at least some of the component redundancies, excessive space, viewing/analysis difficulties, and other drawbacks of conventional arrangements.

SUMMARY OF THE INVENTION

The invention involves an analytical microscope (and analytical microscopy methods) which is intended to at least partially solve the aforementioned problems. To give the reader a basic understanding of some of the advantageous features of the invention, following is a brief summary of preferred versions of the microscope, with reference being made to the accompanying drawing of an exemplary version to assist the reader's understanding. Since this is merely a summary, it should be understood that more details regarding the invention may be found elsewhere in this document. The claims set forth at the end of this document then define the various versions of the invention in which exclusive rights are secured.

Looking to the drawing, the exemplary microscope 100 includes a sample stage 102 whereupon a sample 104 may be provided for microscopic analysis. A first light source 106 provides a first incident light beam 108 to be directed onto the sample 104 (preferably via a first reflector 110 and/or other optical elements, to be discussed below). The first incident light beam 108 induces the escape of first exiting light 112 from the sample 104, with the first exiting light 112 having a first set of wavelengths. For example, the first light source 106 may be an ultraviolet light source (i.e., at wavelengths between 4 to about 400 nanometers) which induces the emission of first exiting light 112 from the sample 104 in visible wavelengths, in which case the microscope 100 provides a UV fluorescence mode for imaging the sample 104.

Similarly, a second light source 114 provides a second incident light beam 116 to be directed onto the sample 104, preferably via a second reflector 118 and/or other optical elements such as the third and fourth reflectors 120 and 122, to be discussed below. The second incident light beam 116 induces the escape of second exiting light 124 from the sample 104, with the second exiting light 124 having a second set of wavelengths. The second incident light beam 116 preferably contains at least some wavelengths different from those in the first incident light beam 108 so that the incident beams provide different modes for analyzing the sample 104. For example, while the first incident light beam 108 may be in UV wavelengths to generate the emission of visible wavelength-shifted first exiting light 112, the second incident light beam 116 may be provided by a laser 114 emitting at one or more wavelengths tailored to generate second exiting light 124 from the sample 104 having a high degree of visible Raman emissions.

A collection lens 126 then collects both the first and second exiting light 112 and 124 from a shared light collection path 128 leading from the sample 104. The collection lens 126 provides the collected light to a first display means 130/132 for displaying the first exiting light 112, and to a second display means 134 for displaying the second exiting light 124 (both to be discussed in greater detail below). Thus, both modes of imaging/analysis provided by the first and second light sources 106 and 114—e.g., UV fluorescence and Raman analysis—can be provided by the same microscope 100. However, as previously noted, it can be difficult to have optical elements such as the collection lens 126 accurately pass/focus exiting light across a wide range of wavelengths B for example, a collection lens 126 which accurately focuses visible light will usually not work well with UV light. Thus, the collection lens 126 is preferably situated such that it need not transmit to the sample 104 any incident light beam 108/

116 which the collection lens 126 cannot usefully process. In the exemplary microscope 100, this is accomplished by providing the collection lens 126 a dark field objective lens, such that the first incident light beam 108 is non-coincidentally directed about the collection lens 126. More specifically, as illustrated in the drawing, the first incident light beam 108 extends along an annular path concentric with, but traveling about the outer perimeter of, the collection lens 126. The dark field illumination of the sample 104 is preferably provided by the first reflector 110 (either alone or in conjunction with a light-blocking mask 136 adjacent the first light source 106), with the first reflector 110 having a nonreflective area 138 (such as an aperture or transparent area) defined within its boundaries and aligned along an axis extending from the sample 104 and collection lens 126. Thus, the first reflector 110 directs the first incident light beam 108 about the perimeter of the collection lens 126, with the collection lens 126 itself being aligned between the nonreflective area 138 and the sample stage 102. At the same time, the first exiting light 112 from the sample 104 is received by the collection lens 126, and may be directed through the nonreflective area 138 of the first reflector 110 to be received by the first display means 130/132.

To better direct the first incident light beam 108 onto the sample 104, a concentrator 140 is provided between the first reflector 110 and the sample stage 102, wherein the concentrator 140 reduces the diameter of the first incident light beam 108 as it travels to the sample 104. The concentrator 140 preferably includes a converging inner passage 142 situated on an axis between the collection lens 126 and the sample stage 102. The passage 142 is bounded by a reflective inner surface 144 such that the first incident light beam 108, after traveling about the perimeter of the collection lens 126 and being received in the concentrator inner passage 142, will concentrate incident light onto the sample stage 102 (and more specifically the sample 104). At the same time, the passage 142 allows exiting light from the sample 104 to pass back through the concentrator 140 to the collection lens 126 without distortion. The concentrator 140 preferably takes the form of a parabolic mirror with a passage 142 centrally formed in its bowl, though it could take the form of a funnel (or other concave converging member) having a reflective inner surface, or a condensing lens or other optical element having a central passage (or other optically transparent region).

Once the first exiting light 112 is emitted through the passage 142 in the concentrator 140 and collected by the collection lens 126, it is directed through the nonreflective area 138 of the first reflector 110 and to the first display means 130/132, which may take a variety of different forms. As examples, where the first exiting light 112 is visible light generated from UV fluorescence, the display means might take the form of a lens 130 or other optical element for allowing direct viewing of the exiting light by a user's eye. Alternatively (or additionally), the first display means may take the form of a video camera 132 or other photosensitive detector(s) (e.g., a CCD array) which images the first exiting light 112 for viewing on a monitor or other display. If the exiting light 112 is not in the visible range, or where it requires processing in order to impart meaning to the information that it encodes, the first display means might take the form of a photosensitive detector (or array of detectors) which convert the light to electric signals, and in turn to visible information, whether in the form of an image (e.g., of non-visible light shifted to the visible range), an electronic display of alphanumeric or pictorial data (e.g., tables, charts, graphs), or another form. For example, if the first exiting light 112 contains the remaining components of a first incident light beam 108 which is at least partially absorbed, scattered, or otherwise altered by the sample 104, the first display means could take the form of a spectrograph (in addition to, or instead of, any spectrograph provided in the second display means 134), thereby allowing identification of the component wavelengths of the first exiting light 112.

If the first exiting light 112 contains some undesired component—for example, where it contains UV light reflected from the sample 104, which is preferably not received by a user's eyes—one or more filters 146 may be interposed between the collection lens 126 and the first display means 130 to remove the unwanted wavelengths. It should be understood that other optical elements (e.g., lenses, reflectors, filters, etc., not shown) for focusing, directing, or otherwise processing the first exiting light 112 may also be provided as needed.

Returning then to the topic of the second incident light beam 116 and its use to provide a second mode of imaging/analysis in addition to the mode provided by the first incident light beam 108, as previously noted, the preferred version of the microscope 100 provides the second incident light beam 116 in the form of laser light suitable for generating Raman emissions from the sample 104 (i.e., wavelength-shifted light scattered from the sample 104). The second light source 114 (laser) is depicted as providing its second incident light beam 116 through beam-expanding optical elements 148, and through generically-depicted supplemental optical elements 150, e.g., beam adjustment lenses/filters, to the fourth reflector 122. The fourth reflector 122 in turn provides the second incident light beam 116 to the third reflector 120, which preferably takes the form of a beamsplitter/dichroic mirror which reflects selected wavelengths and passes others in a manner discussed below. The third reflector 120 then in turn provides the second incident light beam 116 to the second reflector 118 and to the collection lens 126, which directs the beam 116 onto the sample 104. The collection lens 126 also collects the second exiting light 124 (the wavelength-shifted Raman emissions) from the sample 104 and directs them back to the second reflector 118. Thus, the second incident light beam 116 and second exiting light 124 counterpropagate along the shared light collection path 128 with a common focal point at the sample 104. The second reflector 118 then provides the second exiting light 124 to the third reflector 120, which is designed to reflect the second incident light beam 116 but to pass light of wavelengths about that of the second exiting light 124. Thus, the second exiting light 124 is passed through the third reflector 120, through supplemental optical elements 152 (e.g., beam adjustment lenses/filters, if needed), and then into the second display means 134. Here, the second display means 134 is preferably provided as a spectrograph 134, which may include an input lens 154, and which is schematically depicted as including an interferometer 156 and a photosensitive detector 158. The interferometer 156 provides an optical output dependent on the wavelengths present in the second exiting light, and the detector 158 receives this output and generates an electrical signal in response to the detected wavelengths. This electrical signal can then be provided to users in some desired form, e.g., as an electronic display of alphanumeric or pictorial data (e.g., tables, charts, graphs, etc.).

As noted above, while the preferred version of the invention involves a microscope 100 capable of providing both UV fluorescence and Raman imaging/analysis, it should be understood that other modes of imaging/analysis could be implemented in the invention instead, in which case the first and second display means may take different forms. Thus, the invention might allow UV fluorescence imaging in combination with one or more of Raman, infrared, near-infrared, and/or ultraviolet-visible (UV-Vis) spectroscopy (using Fourier Transform or other analysis techniques). Other types of microscopy, such as conventional light microscopy, polarization microscopy, etc. could also or alternatively be implemented. Thus, either or both of the first and second display means may include varying arrangements of ocular lenses (eyepieces), cameras, detectors, etc. depending on the exiting light to be detected and displayed.

In this respect, it is notable that if the first display means is provided in the form of an ocular lens (eyepiece) 130 for direct user viewing of first exiting light 112 generated by UV fluorescence imaging, it is not recommended that Raman imaging/analysis be performed at the same time, since some of the second incident (laser) light beam 116 may possibly reach the first display means 130 and harm the user's vision. Thus, it is preferred that the second reflector 118 be translatable into and out of the shared light collection path 128 such that when it is placed between the collection lens 126 and the first display means 130, all exiting light is effectively diverted to the second display means 134, with the first display means 130 being effectively disabled. Conversely, when the second reflector 118 is removed from the shared light collection path 128, the second incident (laser) light beam 116 is not supplied to the sample 104, and the first display means 130 cannot receive a corresponding laser input. Similar failsafe arrangements are preferably provided in any other versions of the microscope 100 wherein some mode of directly-viewed imaging/analysis is provided in conjunction with some other mode of imaging/analysis which is potentially harmful to a viewer's eyes.

Since the exemplary microscope 100 uses the same objective lens (the collection lens 126) to collect exiting light from the sample 104, the microscope 100 beneficially avoids the need to swap objectives for the UV fluorescence microscopy and Raman analysis modes. Thus, the viewed region of interest on the sample is the same as the one that is spectroscopically analyzed.

Further advantages, features, and objects of the invention will be apparent from the following detailed description of the invention in conjunction with the associated drawing.

BRIEF DESCRIPTION OF THE DRAWINGS

THE FIGURE is a schematic depiction of a preferred exemplary version of the invention, wherein a microscope 100 provides viewing of fluorescence emitted by a sample 104 through an eyepiece 130 or camera 132 from incident UV light 108 emitted by a first light source 106, and which also provides Raman analysis via a spectrograph 134 which measures Raman emissions 124 from the sample 104 induced by a laser 114.

DETAILED DESCRIPTION OF PREFERRED VERSIONS OF THE INVENTION

To expand on the discussion in the foregoing Summary of the Invention, the microscope 100 described above can be constructed by combining the components of preexisting microscopes and spectrometers, and making adaptations where necessary to ensure compatibility. As an example, the microscope 100 can be constructed by adapting a Nicolet Almega model XR dispersive Raman spectrometer (Thermo Electron, Madison, Wis. USA) to include components of an Olympus BX-51 microscope (Olympus America, Melville, N.Y. USA). The light source 106 is selected/constructed for ultraviolet illumination using the Olympus 5-UR720 illuminator, Olympus 5-UL155 lamp housing, Olympus 5-UT150 power supply, and Olympus B-B192 U lamp. The objective 126 is chosen as needed to obtain the desired magnification and working distance; for example, the Olympus 1-UN534 BF/DF Plan Fluorite objective can be chosen for 100× magnification at 0.31 mm working distance, or the Olympus 1-UN345 BF/DF Plan Fluorite objective can be chosen for 100× magnification at 3.4 mm working distance. However, it is emphasized that a wide variety of spectrometers/microscopes and components other than (or in addition to) these may be used. Filters 146 may then be chosen as desired for use in the exiting light beam 112, with a variety of filters being widely available (e.g., from Omega Optical, Brattleboro, Vt. USA).

It should be understood that the analytical microscope 100 is merely an exemplary one, and the invention encompasses a variety of microscopes different from the one described above and shown in the drawings. Following is a list of exemplary modifications that could be made to the microscope 100.

As noted previously, modes of imaging/analysis other than (or in addition to) UV fluorescence imaging and Raman spectrometric analysis could be used, e.g., classical optical microscopy, polarization microscopy, infrared spectrometry, UV-Vis spectrometry, etc. However, UV fluorescence imaging and Raman spectrometric analysis provide a particularly beneficial combination because many biological materials (e.g., tissue samples), crystalline materials (e.g., semiconductor wafers), and other materials of interest either naturally fluoresce or can be stained to fluoresce under UV light. At the same time, Raman spectrometry may provide useful compositional information about the region of the sample being viewed, and is tolerant of water or other infrared-absorptive substances present in the sample (whereas IR spectrometry may provide limited information where water is present).

Since the drawing of the microscope 100 is merely a schematic one, it should be kept in mind that the microscope 100 can be constructed with a radically different appearance. A variety of additional and/or different optical elements might be employed, e.g., further lenses, reflectors, filters, etc. might be used depending on how the incident and exiting light is to be tailored; optical elements may be replaced with other types of optical elements having equivalent performance (e.g., lenses may be replaced by equivalent reflectors); sets of optical elements might be replaced by single optical elements providing all performance features of the original elements (e.g., filtration features might be incorporated into lenses); and conversely single optical elements might be replaced by sets of optical elements which provide the same or similar performance. Incoming and outgoing beam paths for incident and exiting light may vary widely from those shown, particularly if different reflector arrangements or additional reflectors are used. For example, a more compact arrangement might be attained by inverting the reflector 118 and providing the first light source 106, spectrograph 134, and intermediate components adjacent the first light source 106.

Additional features and enhancements might also be provided, for example, features of prior analytical microscopes such as the one described in U.S. Pat. No. 6,661,509, such as beam alignment features and computer-assisted viewing and analysis optimization. It is also possible that components of the microscope could be combined, e.g., the first and second display means 132 and 134 might be at least partially combined, as by providing both the microscopic image captured by the first display means and the spectra captured by the second display means on the same screen of a computer monitor or other electronic display.

It is emphasized that the invention is not intended to be limited to the preferred versions of the invention discussed above, but rather is intended to be limited only by the claims set out below. Thus, the invention encompasses all different versions that fall literally or equivalently within the scope of these claims.

What is claimed is:

1. An analytical microscope comprising:
   a. a sample stage whereupon a sample may be provided for analysis;
   b. a first light source emitting ultraviolet light;
   c. a second light source emitting laser light, the second light source being oriented to provide an incident laser light beam toward the sample stage;
   d. a first reflector having a reflective area surrounding a nonreflective area, the first reflector being oriented to receive ultraviolet light from the first light source and reflect an incident ultraviolet light beam toward the sample stage;
   e. a collection lens adjacent the sample stage and being oriented to collect light exiting therefrom, the collection lens being situated between the nonreflective area of the first reflector and the sample stage whereby the incident ultraviolet light beam surrounds, but is at least substantially noncoincident with, the collection lens;
   f. a detector receiving collected light from the collection lens and generating an electrical signal in response to detected wavelengths therein; and
   g. display means for receiving collected light from the collection lens and generating a visual display therefrom.

2. The analytical microscope of claim 1 wherein the nonreflective area of the first reflector is oriented to receive the collected light from the collection lens and pass the collected light to the display means.

3. The analytical microscope of claim 1 wherein the nonreflective area of the first reflector is an aperture defined within the first reflector.

4. The analytical microscope of claim 1 further comprising a concentrator between the first reflector and the sample stage, wherein the concentrator reduces the diameter of the incident ultraviolet light beam as the incident ultraviolet light beam travels to the sample stage.

5. The analytical microscope of claim 4 wherein the concentrator is also located between the collection lens and the sample stage.

6. The analytical microscope of claim 4 wherein the concentrator has an passage defined therein, the passage being situated on an axis between the collection lens and the sample stage.

7. The analytical microscope of claim 1 further comprising a filter situated along an axis extending between:
   a. the collection lens,
   b. the nonreflective area of the first reflector, and
   c. the display means, wherein the filter blocks transmission of ultraviolet light from the first light source.

8. The analytical microscope of claim 1 wherein the display means generates a visual display from different wavelengths of collected light than the detected wavelengths from which the detector generates an electrical signal.

9. The analytical microscope of claim 1 further comprising a second reflector situated between the collection lens and the display means, wherein the second reflector diverts at least a portion of the collected light to the detector.

10. The analytical microscope of claim 9 wherein the second reflector is provided on a translatable mount which is movable to a location at which the second reflector no longer receives light from the collection lens.

11. The analytical microscope of claim 9 further comprising an interferometer interposed between the second reflector and the detector.

12. The analytical microscope of claim 1 further comprising an interferometer interposed between the collection lens and the detector.

13. An analytical microscope comprising:
   a. a first light source configured to provide a first incident light beam;
   b. a first reflector bounding a nonreflective area, wherein the first reflector is configured to receive the first incident light beam from the first light source and further configured to direct the first incident light beam to a sample;
   c. a concentrator configured with a converging inner passage bounded by a reflective surface, wherein the concentrator receives the first incident light beam at the reflective surface and reduces the diameter of the first incident light beam as the first incident light beam travels through the converging inner passage to the sample, thereby generating a first exiting light from the sample having a first set of wavelengths;
   d. a second light source configured to provide a second incident light beam onto the sample, thereby generating a second exiting light from the sample having a second set of wavelengths, wherein the second incident light beam contains at least some wavelengths different from those in the first incident light beam and the first exiting light;
   e. a collection lens configured to allow the first incident light beam to travel about the perimeter as directed by the first reflector, wherein the collection lens is also aligned with the nonreflective area of the first reflector so as to enable collection along a shared light collection path, the first exiting light in addition to the second exiting light as induced from the sample;
   f. first display means for displaying the first exiting light, the first display means receiving the first exiting light from the collection lens; and
   g. second display means for displaying the second exiting light, the second display means receiving the second exiting light from the collection lens.

14. The analytical microscope of claim 13 wherein the first exiting light travels from the collection lens to pass through the first reflector.

15. The analytical microscope of claim 13 wherein the first reflector has an aperture defined therein through which the first exiting light travels.

16. The analytical microscope of claim 13 wherein the nonreflective area receives and passes the first exiting light.

17. The analytical microscope of claim 13 further comprising:
   a filter oriented along an axis extending from the collection lens and the nonreflective area, with the nonreflective area being situated between the filter and the collection lens, wherein the filter passes the first exiting light from the collection lens to the first display means while blocking transmission of at least some of the wavelengths present in the first incident light beam.

18. The analytical microscope of claim 13 further comprising a second reflector situated in the shared light collection path leading from the sample, wherein the second reflector diverts at least a portion of the second exiting light to the second display means.

19. The analytical microscope of claim 18 wherein the second reflector is translatable into and out of the shared light collection path.

20. The analytical microscope of claim 18 wherein the second display means includes an interferometer.

21. An analytical microscopy method comprising:
   a. directing a first light beam about the perimeter of a collection lens;
   b. redirecting through a converging inner passage, the received first light beam by a reflective area that bounds the converging inner passage so as to illuminate a sample and generate a first exiting light therefrom;
   c. directing a second light beam onto the sample to generate a second exiting light therefrom, wherein:
      (1) the second light beam contains at least some wavelengths different from those in the first light beam, and
      (2) the second exiting light contains at least some wavelengths different from those in the first exiting light;
   d. collecting both the first and second exiting light from a shared light collection path leading from the sample back through the converging inner passage, the light collection path including a collection lens, wherein the first incident light beam is non-coincidentally situated about the light collection path; and
   e. displaying the collected first and second exiting light to a user.

22. The analytical microscopy method of claim 21 wherein:
   a. the first and second incident light beams are provided to the sample at different times;
   b. the first incident light beam consists of light at ultraviolet wavelengths; and
   c. the second incident light beam consists of laser light.

23. The analytical microscopy method of claim 21 wherein the first and second incident light beams are provided to the sample at different times by interposing a second reflector in the shared light collection path, the second reflector supplying the second incident light beam to the sample.

* * * * *